United States Patent [19]

Stoller

[11] Patent Number: 4,616,657
[45] Date of Patent: * Oct. 14, 1986

[54] DIAPHANOSCOPY APPARATUS

[75] Inventor: Milton Stoller, West Hartford, Conn.

[73] Assignee: The First National Bank of Boston, Boston, Mass.

[*] Notice: The portion of the term of this patent subsequent to Aug. 28, 2001 has been disclaimed.

[21] Appl. No.: 621,194

[22] Filed: Jun. 15, 1984

Related U.S. Application Data

[63] Continuation of Ser. No. 399,865, Jul. 19, 1982, abandoned.

[51] Int. Cl.⁴ .................................................. A61B 6/12
[52] U.S. Cl. ...................................... 128/664; 128/665
[58] Field of Search ........................................ 128/4–8, 128/23, 665, 303.1; 362/32, 166–168, 321; 358/98, 81, 110, 82, 113

[56] References Cited

U.S. PATENT DOCUMENTS

| | | | |
|---|---|---|---|
| 738,707 | 9/1903 | Van Nort | 362/321 |
| 3,136,310 | 6/1964 | Meltzer | 128/6 |
| 3,710,011 | 1/1973 | Altemus et al. | 178/5.4 R |
| 3,748,471 | 7/1973 | Ross et al. | 250/333 |
| 3,994,591 | 11/1976 | Gibbard | 356/178 |
| 4,048,493 | 9/1977 | Lee | 250/205 |
| 4,086,616 | 4/1978 | Catano et al. | 358/81 |
| 4,123,172 | 10/1978 | French | 358/188 |
| 4,125,858 | 11/1978 | Hounsfield et al. | 358/82 |
| 4,170,987 | 10/1979 | Anselmo | 128/665 |
| 4,212,306 | 7/1980 | Mahmad | 128/665 |
| 4,223,995 | 9/1980 | Fletcher | 356/418 |
| 4,253,447 | 3/1981 | Moore et al. | 128/6 |
| 4,259,948 | 4/1981 | Urban | 128/6 |
| 4,261,344 | 4/1981 | Moore et al. | 128/6 |
| 4,286,602 | 9/1981 | Grey | 128/665 |
| 4,290,433 | 9/1981 | Alfano | 128/665 |
| 4,312,357 | 1/1982 | Andersson et al. | 128/665 |
| 4,331,132 | 5/1982 | Mukasa | 128/6 |
| 4,365,307 | 12/1982 | Tatsuwaki et al. | 364/557 |
| 4,467,812 | 8/1984 | Stoller | 128/664 |

FOREIGN PATENT DOCUMENTS 2022244 12/1979 United Kingdom .
2068537 8/1981 United Kingdom .

OTHER PUBLICATIONS

"Color Display System", IBM Technical Disclosure Bulletin, vol. 10, No. 3, Aug. 1967.

Primary Examiner—Edward M. Coven
Assistant Examiner—Max F. Hindenburg

[57] ABSTRACT

A non-destructive testing technique, particularly suitable for the non-invasive examination of human body tissue, wherein the object of interest is sequentially transilluminated within light having different wavelengths. Apparatus for practicing the technique alternately generates light of different colors and the light which passes through the tissue is detected by a video system synchronized with the source of the different wavelength light. The video system provides information bearing signals to data processing circuitry which determines the transmissivity at each wavelength of each point of the object within the viewing field.

20 Claims, 6 Drawing Figures

DIAPHANOSCOPY APPARATUS

This is a continuation of application Ser. No. 399,865, filed July 19, 1982, now abandoned.

BACKGROUND OF THE INVENTION (1) Field of the Invention

The present invention relates to non-destructive testing and particularly to a medical diagnostic technique which requires neither invasion of the body or the use of ionizing radiation. More specifically, this invention is directed to transillumination apparatus and especially to apparatus for sequentially passing light at a plurality of wavelengths through an object and creating a display which is indicative of the amount of absorption at each point in the object of the different wavelengths. Accordingly, the general objects of the present invention are to provide novel and improved apparatus of such character.

(2) Description of the Prior Art

While not limited thereto in its utility, the present invention has particular significance as a breast examination device and method. At the present time there is no accepted procedure, other than palpation by a physician, which may be employed for the routine screening of patients, particularly those under the age of fifty, in an effort to diagnose breast cancer. The most widely accepted current diagnostic technique comprises mammography which, because it requires the use of ionizing, i.e., x-ray, radiation, is customarily employed only subsequent to palpation having revealed an apparent abnormality.

Other non-invasive examination techniques which are available include thermography and echography. Both of these techniques have been found to be of only very limited utility and thus their application has largely been to supplement information obtained through the use of mammography.

It has also been proposed to utilize transillumination i.e., the passing of light through tissue, in order to diagnose abnormalities. Prior transillumination techniques and apparatus are disclosed in U.S. Pat. Nos. 3,127,115, 3,371,202, 3,527,932, 3,674,008, 3,711,700, 3,732,416, 3,769,963, 4,077,399, 4,212,30 and 4,286,602. Transillumination, which is also known in the art as diaphanography or diaphanoscopy, is also discussed in Russian Pat. Nos. 279,879 and 591,178 as well as the publication "Diaphanologie mammaire" C. Gros et al which appeared in J. Radiol Electrol., 1972, Vol. 53, No. 4, pp. 297-306 and the article "Etude diphanoscopique des alteration dystrophiques du sein" by C. Di Maggio et al which appeared in Senologia, June 1978, No. 2, pp. 69-71. The potential advantages of transillumination versus the above-mentioned other non-invasive examination techniques are discussed in detail in U.S. Pat. No. 4,286,602.

Initial efforts to employ transillumination relied upon visual observation of the light which passed through the tissue under study. These efforts were lagely unsuccessful since the human eye is not sensitive to the wavelengths which pass through the human body tissue, i.e., principally wavelengths in the range of 600 to 1500 nanometers. Light having a wavelength below 600 nanometers is largely absorbed by human body tissue while light at wavelengths above 1500 nanometers is largely absorbed by water in the tissue. The difficulty in obtaining useful information by visual observation was increased by the fact that the examination had to be performed in a darkened room and it is well known that the sensitivity of the eye to light having a wavelength within the range of interest decreases in a dark environment.

The major problems incident to visual observation were overcome when infrared light sensitive film became available. However, the use of photographic techniques employing infrared film, like the use of x-rays, does not provide information in real time. Further, since the light source and tissue under examination must be manipulated in order to insure that all regions within the tissue will be seen, and if necessary or desirable seen from different viewing angles, an examination which included recording information on film required either the taking of many pictures or was very time-consuming in that the patient had to wait while the initially taken pictures were developed and viewed so that additional pictures could be taken if necessary.

A recent improvement in transillumination technology employs a TV camera which is sensitive to light in the red and near infrared regions, i.e., in the range of 600 to perhaps 1200 nanometers. The use of a TV camera permits real time imaging and provides results which are believed to be at least comparable to those achieved through mammography but without the use of ionizing radiation. Nevertheless, there is a desire to enhance the capability of presently available transillumination devices and particularly to form an image characterized by tissue differentiation, i.e., to provide output information which is indicative of the type of tissue being illuminated.

SUMMARY OF THE INVENTION

The present invention comprises a novel and improved transillumination technique, particularly a method well suited for the examination of body tissue, and apparatus for use in the practice of that novel technique. In accordance with the present invention the tissue or other object being examined is illuminated, in sequential fashion, with light of different wavelengths. Information commensurate with the light which passes through the tissue at each illumination wavelength is stored and the stored information subsequently employed to produce an image which represents the absorption characteristics or the tissue which has been illuminated.

Apparatus in accordance with the present invention includes a source of transillumination light at different frequencies or within different pre-selected bands of frequency. In accordance with one embodiment, the light source provides light in the red and near infrared regions. The tissue under examination is sequentially illuminated by the different frequency light. The light which passes through the tissue is sensed by a video camera synchronized with the light source. The output of the camera is thus a series of signal corresponding to images of the tissue as illuminated by the light at the different sequentially applied wavelengths. These video signals are separately stored and subsequently employed to form a composite image.

Also in accordance with the preferred embodiment, wherein the tissue is alternately transilluminated by light in two separate frequency bands, the information commensurate with the stored images is employed to produce a display wherein each point of the display contains information characteristic of the ratio of the light within each frequency band which has passed through the tissue at a corresponding point. Thus, by way of example, a color may be assigned to each ratio and a multi-color image formed.

BRIEF DESCRIPTION OF THE DRAWING

The present invention may be better understood and its numerous objects and advantages will become apparent to those skilled in the art by reference to the accompanying drawing wherein.

DESCRIPTION OF THE PREFERRED EMBODIMENT

Figure 1:
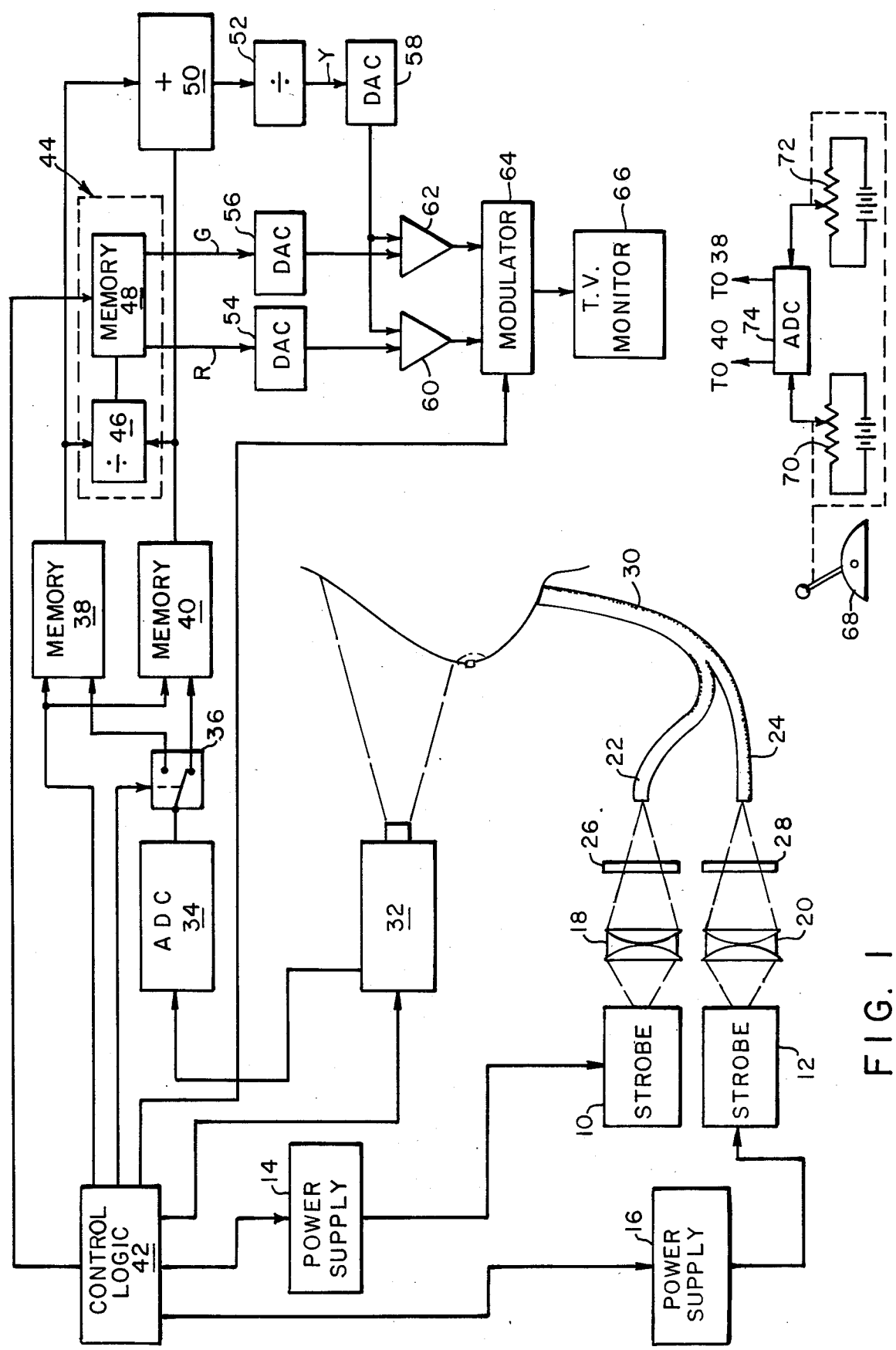
FIG. 1 is a functional block diagram of apparatus in accordance with a first embodiment of the invention.

With reference now to the figures, in the disclosed embodiment light in the red and near infrared spectra is employed for transilluminating human body tissue. Light at the different wavelengths chosen will be absorbed by the tissue as a function of wavelength and tissue type. In accordance with one embodiment of the present invention "white" light is generated by a pair of strobe lights 10 and 12. The strobe lights 10 and 12 include flash lamps which generate light in a comparatively broad spectrum which includes the red and near infrared regions. The strobe lights 10 and 12 may comprise commercially available xenon flash tubes. Strobe lights 10 and 12 are respectively controlled by power supplies 14 and 16 which, in response to input commands, apply trigger pulses to the flash tubes whereby the gas in the tubes will ionize and a capacitor will discharge through the tubes producing a light pulse of short duration. In accordance with one embodiment of the invention the duration of the light pulses produced by strobe lights 10 and 12 was ten microseconds and the output power of the lights was one joule.

The light produced by strobe lights 10 and 12 is respectively collected by condensing lens systems 18 and 20 which focus the light at the ends of respective fiber optic bundles 22 and 24. Filters 26 and 28 are disposed in the light path between respective of strobe lights 10 and 12 and the associated fiber optic bundles 22 and 24. Filter 26, in the embodiment being described, will pass only wavelengths in the 650 to 750 nanometer, i.e., red, region. Filter 28 will pass light only in the 750 to 850 nanometer, i.e., near infrared, region. The fiber optic bundles 22 and 24 are combined into a single bundle 30. In examining a breast, as depicted in the drawing, the free end of fiber optic bundle 30 is placed in contact with the skin to produce a source of transilluminating light. In the manner to be described in greater detail below, the strobe lights 10 and 12 are alternately energized in synchronism with a video system whereby the tissue of interest will be transilluminated first with red light and then with light in the near infrared region.

During transillumination a video camera 32 is focused on the breast or other object being examined. In the embodiment being described the camera 32 will include a silicon face plate tube that is responsive in the region from 650 nanometers to 900 nanometers. The camera tube may, for example, comprise a silicon diode array type device available from RCA under the trademark "Ultricon". The short bursts of light received by camera 32 have the effect of discharging, in varying degrees, the surface of the video camera tube. Scanning of the tube surface by an electron beam produces, in the conventional manner, a video output signal. This analog output signal is delivered as the input to an analog-to-digital converter 34. The digitally coded signals from converter 34 are alternately supplied, via a switch 36, to a pair of frame memories 38 and 40. The memories 38 and 40 may, for example, comprise dynamic memory elements having eight bits of memory for each picture location, i.e., each pixel.

Operation of the circuitry described above is under the supervision of controller logic 42. Controller 42 comprises a clock, down counter and gates and provides the vertical and horizontal synchronizing signals to camera 32. Thus, referring to FIG. 2, during a first vertical retrace time of the electron beam in camera 32 controller 42 will supply a gating pulse 14' to the power supply 14 which will cause the flash tube of strobe light 10 to fire thereby producing an intense burst of light which lasts a few microseconds. As discussed above, this light will be connected by the condensing lens system 18, filtered by filter 26 and the resulting "red" light delivered to the end of fiber optic bundle 30 which is in contact with the patient. The logic circuit 42 will also control the operation of switch 36, which will typically be an electronic switch, such that the digitally encoded signal produced during a single frame of scanning of the tube in camera 32 will be loaded into memory 38. Memory 38 will thus contain information commensurate with the intensity of the red light which has passed through the tissue being examined i.e., the degree of absorption of light at a first wavelength. The time during which the data is being entered into memory 38, i.e., one frame time, is indicated on FIG. 2 at 38'. During the next frame the vidicon is permitted to fully recharge.

Figure 2:
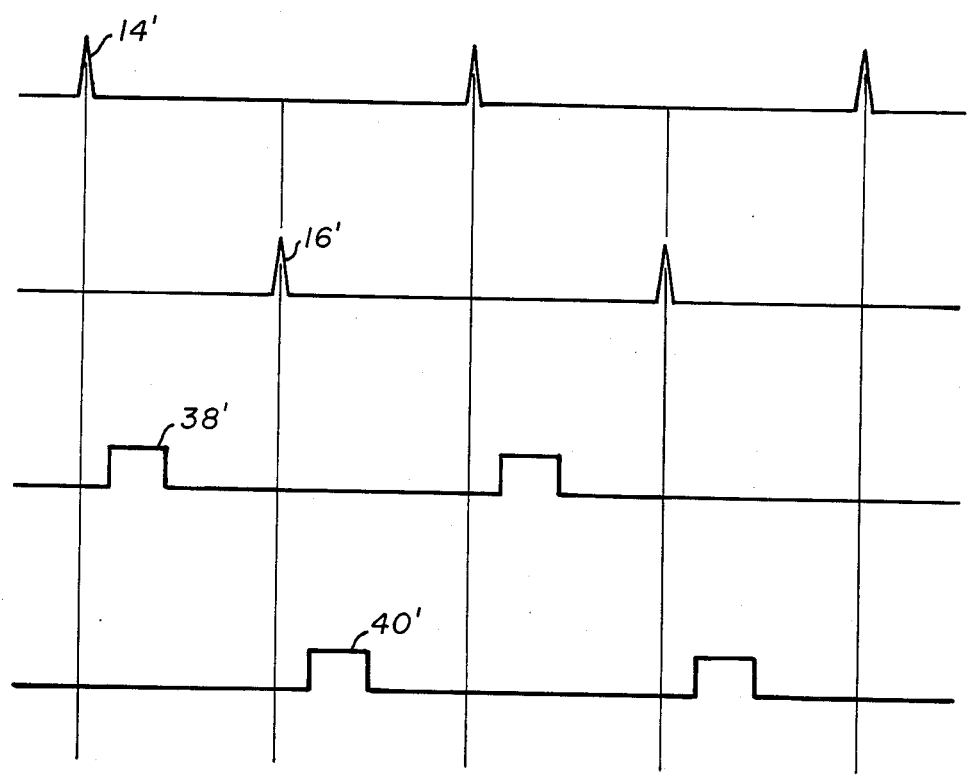
FIG. 2 is a timing diagram which relates to operation of the apparatus of FIG. 1.

During the next, i.e., third, vertical retrace time of camera 32 controller logic 42 will produce an output signal, indicated at 16' in FIG. 2, which causes the firing of the flash tube in strobe light 12. Accordingly, the breast will, during this retrace time, be illuminated with light in the near infrared region, this light being produced from the output of strobe light 12 by filter 28 and delivered to the branch 24 of the bifurcated fiber optic bundle. During the next scanning of the light responsive surface of the video tube of camera 32 the control logic 42 will operate switch 36 so as to deliver the digitally encoded information commensurate with the near infrared light transmitted through the tissue into frame memory 40. The time during which information is entered into memory 40 is indicated in FIG. 2 at 40'. Thus, in the embodiment being described, at the end of four frames of the scanning cycle of video camera 32, the tissue being examined will have been illuminated with light of two different colors and the information commensurate with the intensity of the light at two different wavelengths which has passed through the tissue will be stored in separate memories.

The information in memories 38 and 40 is simultaneously read by an encoder which is indicated generally at 44. In actual practice, encoder 44 will comprise a RAM which functions as a look-up table. To facilitate understanding of the disclosed embodiment of the invention, encoder 44 has been functionally depicted as a divider 46 and a memory 48. The memory 48 will have, for example, $2^8 \times 2^8$ addresses and numbers corresponding to the intensity of two colors, typically red and green, commensurate with ratios of the numbers which may be stored at each pixel in memories 38 and 40 will be stored at the memory locations in memory 48. The data stored in memories 38 and 40 will be read by memory 48 at twice the rate of loading of memories 38 and 40. The numbers stored at the corresponding memory locations in memories 38 and 40 are employed to address memory 48 and memory 48 will produce a pair of color related, digitally coded output signals for each pixel. This is functionally equivalent to dividing the numbers stored at the memory locations in memories 38 and 40 in the divider 46 and employing the thus produced ratio to address memory 48. The numbers which are read out of memory 48 comprise digitally coded chrominance signals which, in the example being described, will correspond to a red "R" intensity and a green "G" intensity.

The numbers read from memories 38 and 40 are also applied to an adder 50 where they are summed. The output of adder 50 is delivered to a divide by two circuit 52. The output of divider 52 is a digitally encoded average luminance or "Y" signal.

The "R" and "G" chrominance signals from memory 48 are converted to analog form by means of digital-to-analog converters 54 and 56 while the average luminance signal is converted to analog form by digital-to-analog converter 58. The outputs of converters 54 and 56 are respectively applied as first inputs to differential amplifiers 60 and 62. The second input to amplifiers 60 and 62 is the luminance signal from converter 58. The combined luminance and chrominance signals appearing at the outputs of amplifiers 60 and 62 are applied to a standard TV modulator 64 which also receives synchronizing signals from controller 42. Modulator 64 provides a composite color video signal which is delivered to a TV monitor 66. This composite signal will, in the customary fashion, provide horizontal sync, color burst and color modulation information for each frame.

It is to be noted that, in the interest of reducing the size of the look-up memory, in one reduction to practice of the invention the encoder 44 looked at the most significant six bits of the signals stored in memories 38 and 40 while the adder 50 looked at all eight bits of the stored data.

It is also to be noted that the present invention may be employed as an analytical tool wherein the ratio of the absorption by the object under examination of light at the transillumination for frequencies at any point of interest may be read out and displayed on monitor 66. To this end a joy stick 68, coupled to potentiometers indicated schematically at 70 and 72, may be employed to provide input signals to an analog-to-digital converter 74. Converter 74 will, in turn, provide address information to memories 38 and 40. When there is coincidence between the addresses from converter 74 and the read-out address of the memories, a spot or cursor will be displayed on monitor 66 and the contents of the memories will be delivered to a microprocessor via buffers. The microprocessor will, pursuant to its instructions, cause an alphanumeric display which may, for example, be the ratio of absorption of the two transilluminating light wavelengths.

Figure 3:
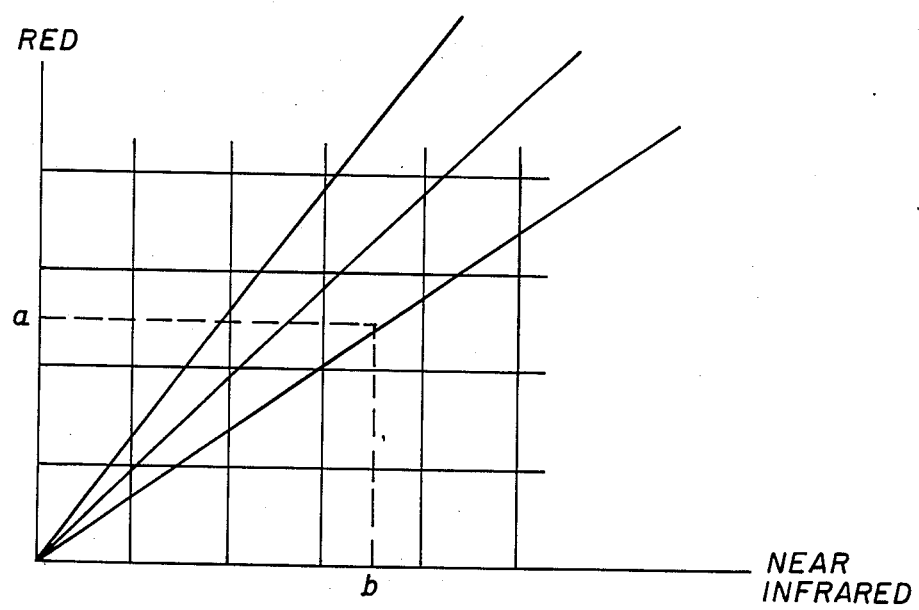
FIG. 3 is a graphical presentation which will facilitate understanding of the operation of the apparatus of FIG. 1.

FIG. 3 may be considered a graphical representation of the function of encoder 44. The ratio a/b of the numbers commensurate with the intensity of the light at the two transillumination wave lengths which passes through the tissue under examination defines straight line curves. Each discrete curve will have assigned thereto chrominance values corresponding to red and green signal amplitude.

The amount of absorption of different color light varies with the nature of the tissue being transilluminated even in the case of normal tissue. Accordingly, it has been found desirable to initially perform a "normalizing", i.e., a balancing, step when practicing the present invention. Since the absorption of light in the red and near infrared regions will vary with the characteristics of the tissue under examination, for example as a function of whether the tissue is glandular or fatty, an initial adjustment will typically be made so that normal tissue will be displayed as a pre-selected color or colors. Thus, in a typical case, the image of tissue which has been determined to be normal for the patient being examined may be displayed as a white and black image while abnormalities may be represented by colors. The color white will be commensurate with a pre-selected a/b ratio (FIG. 3) and, accordingly, the adjustment, i.e., the "normalizing", may be accomplished by varying the voltages applied to flash tubes 10 and 12 (FIG. 1) to thereby vary the intensity of the two colors of light. It is also possible to separate the light passing through the tissue into two beams which are subsequently filtered and detected, the adjustment being made to the resulting signals. A further possibility would be to employ two vidicons and selectively vary the gain thereof to achieve the "normalization".

Figure 4:
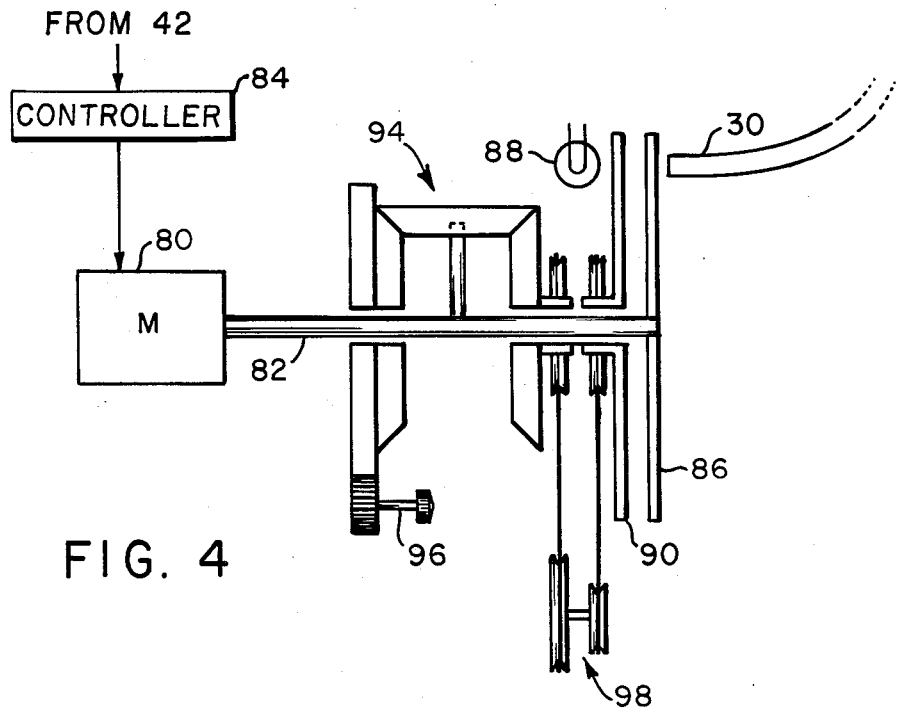
FIG. 4 is a schematic side-elevation view of a light source for use in the apparatus of FIG. 1.
Figures 5A, 5B:
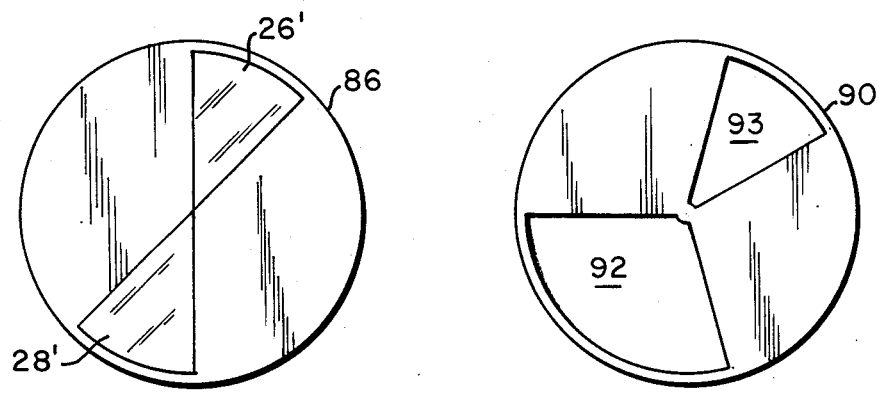
FIGS. 5A and 5B respectively depict shutter and filter devices for use in the apparatus of FIG. 4.

In accordance with the preferred embodiment of the invention the above-discussed step of "normalizing" is achieved through use of the apparatus of FIGS. 4 and 5 in place of the pair of flash lamps 10 and 12 and their associated power supplies, lenses and filters as shown in FIG. 1. In the apparatus of FIG. 4 a motor 80 rotates a drive shaft 82 at a speed determined by a controller 84, controller 84 being responsive to output pulses received from control logic 42. A disc 86 is mounted on shaft 82 for rotation therewith. Disc 86 is provided with a pair of equal size and oppositely disposed windows. Filters, which correspond respectively to filters 26 and 28 of the FIG. 1 embodiment, are respectively mounted in the windows in disc 86 as indicated at 26' and 28'. A source of white light, indicated schematically at 88, is positioned such that the light emitted therefrom will alternately pass through filters 26' and 28' as disc 86 rotates. The end of the fiber optic bundle 30 is located in alignment with light source 88. Thus, as disc 86 is rotated the fiber optic bundle will alternately receive light in the red and near infrared regions. The speed of motor 80 will be selected such that the tissue under examination will alternately be transilluminated with the different color light in synchronism with the operation of camera 32, i.e., during a first frame the tissue will be illuminated with red, during a second frame the vidicon will be read out, during the third frame the vidicon screen will be recharged, during the fourth frame the tissue will be illuminated with infrared, during a fifth frame the infrared data will be read out of the vidicon, during the sixth frame the vidicon screen will be recharged, and the process will thereafter repeat.

As noted above, the "normalization" procedure will typically be performed so as to cause all normal tissue to appear in white on a black background. Thus, at the onset of each examination, the apparatus will be adjusted so that transillumination of the patient's normal tissue will result in camera 32 receiving light of equal intensity during the illumination of the tissue with both red and infrared. This normalization is achieved by mounting a shutter 90 for rotation with disc 86. Shutter 90 is provided with a pair of different size windows 92 and 93, window 93 being substantially equal in size and shape to the filters 26' and 28'. By means of a differential, indicated generally at 94, the differential being driven from shaft 82, shutter 90 is manually rotatable relative to disc 86 so that one of the filters 26' or 28' may be partially covered while the other remains fully uncovered. This relative rotation is achieved via a control input 94 which can be employed, in the known manner, to either advance or retard shutter 90 relative to disc 86 while the two discs are rotating at the same speed. A speed reduction mechanism 98, in the form of pulleys and belts, is interposed between differential 94 and shutter 90 for the purpose of causing the shutter to rotate at the same speed as the filter carrying disc.

While the present invention has been described as alternately illuminating the object under examination with light or two different wavelengths, it will be understood that the invention is not limited to transillumination with light of only two different colors or to the use of light within the frequency ranges discussed. Accordingly, while preferred embodiments have been shown and described, various modifications and substitutions may be made thereto without departing from the spirit and scope of the invention. Thus, it is to be understood that the present invention has been described by way of illustration and not limitation.

What is claimed is:

1. Apparatus for the non-invasive and non-destructive examination of tissue comprising:
    means for illuminating the tissue to be examined with pulses of light, the light pulses which serially illuminate the tissue exclusively including light having preselected different wavelengths;
    detector means for sensing the light which passes through the tissue during illumination thereof, said detector means sequentially generating signals commensurate with the energy content of transilluminated light at least at a first and a second of said preselected wavelengths;
    balancing means for adjusting the energy content of the light pulses including light at the first wavelength received by said detector means relative to the energy content of the light pulses including light at the second wavelength received by said detector means;
    first memory means coupled to said detector means and said illuminating means for separately recording signals sequentially generated by said detector means and commensurate with light at the first wavelength and the second wavelength which has been received by said detector means;
    second memory means for storing display correlated data information commensurate with a plurality of ratios of signals commensurate with light at the said first and second wavelength which may be recorded in said first memory means;
    means for reading stored information from said second memory means, said reading means being responsive to at least a pair of said separately recorded signals commensurate with the energy content of the light at the first and second wavelengths which has been sensed by said detector means during illumination of the same point in the tissue under examination, said display correlated data information thereby being read from said second memory means as a function of a pair of signals separately recorded in said first memory means; and
    means responsive to the information read from said second memory means for producing an image which represents the absorption characteristics of the tissue at the first and second wavelengths.

2. The apparatus of claim 1 wherein said means for producing an image comprises:
    television monitor means, said display correlated data information being delivered as a modulating input to said monitor means.

3. The apparatus of claim 2 wherein said detector means comprises:
    television camera means; and
    means for synchronizing said camera means with said illuminating means whereby said camera means will sequentially generate signals commensurate with images corresponding to the illumination of the tissue with light including the first and the second wavelengths, each image being comprised of a plurality of points.

4. The apparatus of claim 1 wherein said detector means comprises:
    television camera means; and
    means for synchronizing said camera means with said illuminating means whereby said camera means will sequentially generate signals commensurate with images corresponding to the illumination of the tissue with light including the first and the second wavelengths, each image being comprised of a plurality of points.

5. The apparatus of claim 4 wherein said detector means further comprises:
    means for encoding the signals sequentially generated by said camera means; and
    means for delivering said encoded sequentially generated signals to simultaneously addressable memory locations of said first memory means.

6. The apparatus of claim 3 wherein said detector means further comprises:
    means for encoding the signals sequentially generated by said camera means; and
    means for delivering said encoded sequentially generated signals to simultaneously addressable memory locations of said first memory means.

7. The apparatus of claim 1 wherein said illuminating means comprises:
    a board spectrum light source, the light produced by said source including the said first and second wavelengths; and
    controllable filter means, said filter means sequentially passing light within frequency bands which respectively include light at the first and second wavelengths.

8. The apparatus of claim 7 wherein said filter means includes:
    at least a pair of filter elements; and
    means for imparting motion to said filter elements whereby said filter elements are individually and serially placed in the path of light produced by said light source.

9. The apparatus of claim 8 wherein said balancing means comprises:
    means for controlling the amount of light transmitted through at least one of said filter elements.

10. The apparatus of claim 9 wherein said controlling means comprises:
   shutter means, said shutter means moving in synchronism with said filter elements; and
   means for adjusting the relative position of said shutter means and at least one of said filter elements.

11. The apparatus of claim 10 wherein said illuminating means further comprises:
   flexible light transmitting means, said light transmitting means having a receiving end positioned in registration with said shutter means, said transmitting means having an output end which may be placed in proximity to the tissue being examined.

12. The apparatus of claim 11 wherein said detector means comprises:
   television camera means; and
   means for synchronizing said camera means with said motion imparting means whereby said camera means will sequentially generate signals commensurate with images corresponding to the illumination of the tissue with light including the first and the second wavelengths, each image being comprised of a plurality of points.

13. The apparatus of claim 12 wherein said detector means further comprises:
   means for encoding the signals sequentially generated by said camera means; and
   means for delivering said encoded sequentially generated signals to simultaneously addressable memory locations of said first memory means.

14. The apparatus of claim 7 wherein said detector means comprises:
   television camera means; and
   means for synchronizing said camera means with said filter means whereby said camera means will sequentially generate signals commensurate with images corresponding to the illumination of the tissue with light including the first and the second wavelengths, each image being comprised of a plurality of points.

15. The apparatus of claim 14 wherein said filter means includes:
   at least a pair of filter elements; and
   means for imparting motion to said filter elements whereby said filter elements are individually and serially placed in the path of light produced by said source.

16. The apparatus of claim 15 wherein said balancing means comprises:
   means for controlling the amount of light transmitted through at least one of said filter elements.

17. The apparatus of claim 16 wherein said controlling means comprises:
   shutter means, said shutter means moving in synchronism with said filter elements; and
   means for adjusting the relative position of said shutter means and at least one of said filter elements.

18. The apparatus of claim 17 wherein said illuminating means further comprises:
   light transmitting means, said light transmitting means having a receiving end position in registration with said shutter means, said transmitting means having an output end which may be placed in proximity to the tissue being examined.

19. The apparatus of claim 6 wherein said illuminating means comprises:
   a broad spectrum light source, the light produced by said source including the first and the second wavelengths;
   filter means, said filter means including at least a pair of filter elements, said filter elements passing light within separated frequency bands; and
   means for imparting motion to said filter means whereby said filter elements are individually and serially placed in the path of light produced by said source.

20. The apparatus of claim 19 wherein said balancing means comprises:
   means for controlling the amount of light transmitted to the tissue being examined through at least one of said filter elements.

* * * * *